(12) United States Patent
Hasuda et al.

(10) Patent No.: US 8,664,598 B2
(45) Date of Patent: Mar. 4, 2014

(54) ELECTRON MICROSCOPE AND SPECIMEN ANALYZING METHOD

(75) Inventors: Masakatsu Hasuda, Chiba (JP); Atsushi Uemoto, Chiba (JP); Toshiaki Fujii, Chiba (JP); Junichi Tashiro, Chiba (JP)

(73) Assignee: SII NanoTechnology Inc. (JP)

( * ) Notice: Subject to any disclaimer, the term of this patent is extended or adjusted under 35 U.S.C. 154(b) by 184 days.

(21) Appl. No.: 12/931,411

(22) Filed: Jan. 28, 2011

(65) Prior Publication Data

US 2011/0186734 A1  Aug. 4, 2011

(30) Foreign Application Priority Data

Jan. 29, 2010  (JP) ................. 2010-019765

(51) Int. Cl.
*H01J 37/29* (2006.01)

(52) U.S. Cl.
USPC .......................................................... 250/310

(58) Field of Classification Search
USPC ................................................ 250/309–311
See application file for complete search history.

(56) References Cited

U.S. PATENT DOCUMENTS

| | | | | |
|---|---|---|---|---|
| 5,525,806 A | * | 6/1996 | Iwasaki et al. | 250/492.21 |
| 6,690,068 B2 | * | 2/2004 | Yamazaki et al. | 257/359 |
| 2004/0188610 A1 | * | 9/2004 | Hirose | 250/310 |
| 2006/0097166 A1 | * | 5/2006 | Ishitani et al. | 250/310 |
| 2008/0073587 A1 | | 3/2008 | Schmidt et al. | 250/492.21 |
| 2008/0087822 A1 | | 4/2008 | Principe | 250/307 |
| 2009/0020698 A1 | * | 1/2009 | Muto et al. | 250/310 |
| 2009/0121158 A1 | * | 5/2009 | Tomimatsu et al. | 250/492.2 |
| 2011/0226948 A1 | * | 9/2011 | Tanaka et al. | 250/307 |

FOREIGN PATENT DOCUMENTS

| | | |
|---|---|---|
| JP | 06231720 | 8/1994 |
| JP | 2004022318 | 1/2004 |
| JP | 2006194743 | 7/2006 |
| JP | 2006294614 | 10/2006 |
| JP | 2007250529 | 9/2007 |
| JP | 2008210702 | 9/2008 |
| JP | 2009026621 | 2/2009 |

OTHER PUBLICATIONS

Abstract, publication No. 2007-200573, publication date Jan. 23, 2006.

\* cited by examiner

*Primary Examiner* — Jack Berman
*Assistant Examiner* — Eliza Osenbaugh-Stewart
(74) *Attorney, Agent, or Firm* — Adams & Wilks

(57) ABSTRACT

An electron microscope has a focused ion beam column positioned relative to an electron beam column so that the focused ion beam substantially perpendicularly intersects the electron beam. A backscattered electron detector is positioned relative to the focused ion beam column so that the direction normal to a detection plane of the backscattered electron detector is substantially perpendicular to the direction of the focused ion beam. The backscattered electron detector is configured and positioned to detect backscattered electrons released in a spread of at least about 70 degrees in width from the surface of the section by irradiation of the section with the electron beam 1*a*.

16 Claims, 4 Drawing Sheets

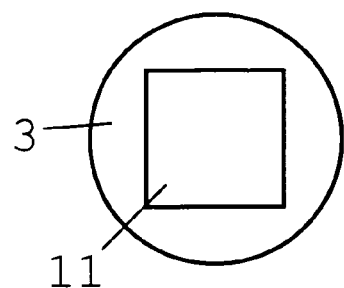
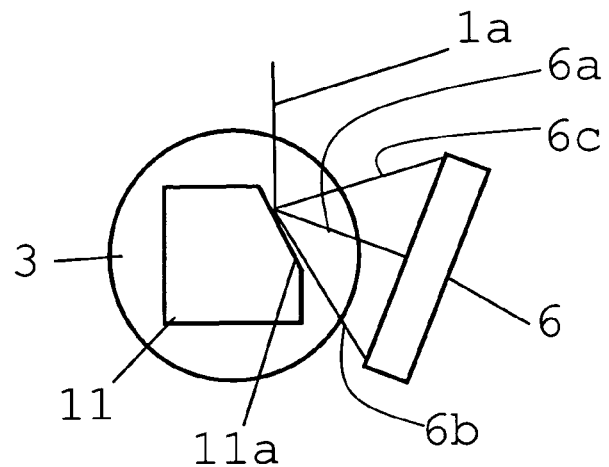
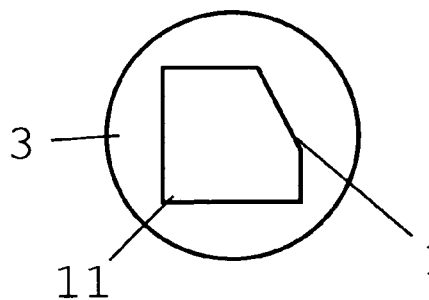
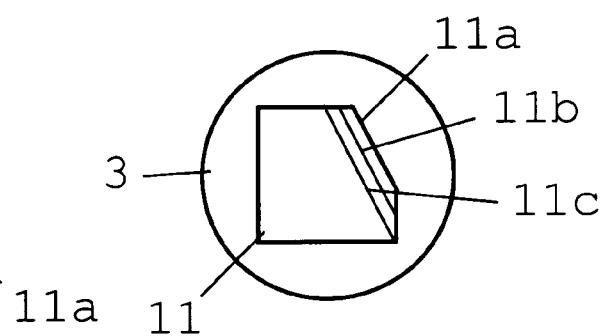
FIG. 4A
FIG. 4C
FIG. 4B
FIG. 4D

ELECTRON MICROSCOPE AND SPECIMEN ANALYZING METHOD

BACKGROUND OF THE INVENTION

1. Technical Field

The present invention relates to an electron microscope that irradiates a specimen with an electron beam, detects backscattered electrons that are released from the specimen, and acquires a diffraction image.

2. Related Art

Conventionally, scanning electron microscopes focus an electron beam, scan a specimen surface, detect secondary electrons produced from the specimen surface, and obtain a secondary electron image. Measuring an electron backscatter diffraction image (electron backscatter pattern (EBSP)) by the scanning electron microscope equipped with a detector that detects backscattered electrons is also known (see JP-A-2007-200573). Thus, it becomes possible to obtain crystal orientation information of the specimen.

However, the crystal orientation information acquired by conventional electron microscopes is information of the vicinity of the specimen surface, and it is often difficult for conventional electron microscopes to obtain information of the specimen interior.

SUMMARY OF THE INVENTION

The present invention has been made in view of these circumstances, and it is an object thereof to provide an electron microscope that can easily acquire crystal orientation information of a specimen interior.

In order to achieve this object, the present invention provides the following means.

The present invention provides an electron microscope, including: an electron beam column for irradiating a specimen with an electron beam; a specimen stage that supports the specimen; a focused ion beam column for irradiating the specimen with a focused ion beam and forming a section; and a scattered electron detector for detecting backscattered electrons produced from the section by irradiation with the electron beam. According to the electron microscope, the section processed by the focused ion beam can be irradiated with the electron beam and the backscattered electrons that are released from the specimen can be detected. Consequently, processing and EBSP measurement can be performed in situ inside the same device, so EBSP measurement can be performed efficiently.

The scattered electron detector of the electron microscope detects a Kikuchi pattern of the backscattered electrons. Thus, EBSP-measured information can be obtained because a Kikuchi pattern can be detected.

An angle formed by the scattered electron detector and the electron beam of the electron microscope is 60 degrees to 150 degrees. Thus, backscattered electrons needed for EBSP measurement can be acquired.

In the above-described electron microscope, the focused ion beam is capable of irradiating the region irradiated by the electron beam. Thus, processing and measurement can be performed without having to move the specimen. Moreover, by processing the section with the focused ion beam, forming a deeper section of the specimen, and irradiating the deeper section with the electron beam, EBSP measurement can be performed with respect to a new section of the specimen interior. Efficiency is good because processing and measurement can be done without having to move the specimen.

In the above-described electron microscope, the focused ion beam substantially perpendicularly intersects the electron beam. Thus, even when the scattered electron detector capable of EBSP measurement and the focused ion beam column are installed in a single specimen chamber, the scattered electron detector and the focused ion beam column do not interfere with each other.

In the above-described electron microscope, the specimen stage has an axis of rotation that is substantially parallel to the focused ion beam. Thus, the electron beam and the orientation of the specimen surface can be adjusted at the time of EBSP measurement.

The electron microscope of the present invention further includes a storage unit that stores backscattered electron detection information of mutually substantially parallel multiple sections of the specimen that have been formed by the focused ion beam. Thus, section formation and measurement of the backscattered electrons can be performed continuously because the electron microscope can store the backscattered electron detection information of the section formed by the focused ion beam, form a new section, and import the backscattered electron detection information of the new section.

The electron microscope of the present invention further includes a transmission electron detector for detecting transmission electrons released from the specimen in the emission direction of the electron beam. Thus, by sectioning the specimen with the focused ion beam and detecting the transmission electrons of the electron beam with which the specimen has been irradiated, a transmission electron image of the specimen can be acquired.

The present invention provides a specimen analyzing method, including: a section forming step of irradiating a specimen with a focused ion beam and forming a section; a detecting step of irradiating the section with an electron beam and detecting backscattered electrons produced from the section; and an image acquiring step of acquiring a backscattered electron image of the section from detection signals of the backscattered electrons. Thus, the crystal orientation of the section formed by the focused ion beam can be analyzed.

In the above-described specimen analyzing method, the section forming step and the detecting step are implemented inside the same specimen chamber. Thus, section formation and detection of the backscattered electrons can be performed efficiently and the specimen can be analyzed.

In the above-described specimen analyzing method, the electron beam scans and irradiates the section. Thus, the crystal orientation of the region of the section irradiated by the electron beam can be analyzed.

In the above-described specimen analyzing method, the focused ion beam is emitted from a direction that is substantially perpendicular to the electron beam. Thus, a section including a direction that is substantially perpendicular to the electron beam can be formed.

In the above-described specimen analyzing method, in the detecting step, backscattered electrons produced from the specimen at an angle of 60 degrees to 150 degrees with respect to the electron beam are detected. Thus, backscattered electrons needed for EBSP measurement can be detected.

In the above-described specimen analyzing method, the section forming step and the detecting step are repeatedly implemented to acquire detection signals of backscattered electrons of mutually substantially parallel multiple sections. Thus, EBSP measurement of new sections of the specimen interior can be performed.

In the above-described specimen analyzing method, crystal orientation information of the multiple sections is obtained from the detection signals of the backscattered electrons of the multiple sections that have been detected, and the crystal orientation information is combined to acquire a three-dimensional crystal orientation mapping of the specimen. Thus, the crystal orientation of the specimen interior can be analyzed.

The present invention provides a specimen analyzing method, further including a lamella making step of processing the specimen into a lamella with the focused ion beam and a transmission electron detecting step of irradiating the lamella with the electron beam and detecting transmission electrons from the lamella. Thus, a transmission electron image of the specimen can be acquired.

In the above-described specimen analyzing method, the specimen is analyzed using the backscattered electron image of the section acquired in the image acquiring step and a transmission electron image acquired in the transmission electron detecting step. Thus, the specimen can be analyzed from plural angles from the crystal orientation information and the information of the transmission electron image.

According to the present invention, the electron microscope can easily acquire crystal orientation information of a specimen interior because the electron microscope is equipped with the scattered electron detector and the focused ion beam column.

BRIEF DESCRIPTION OF THE DRAWINGS

FIG. 4A to FIG. 4D are general diagrams describing specimen processing and observation in the embodiment of the present invention.

DESCRIPTION OF PREFERRED EMBODIMENT

An embodiment of the present invention will be described below.

Figure 1:
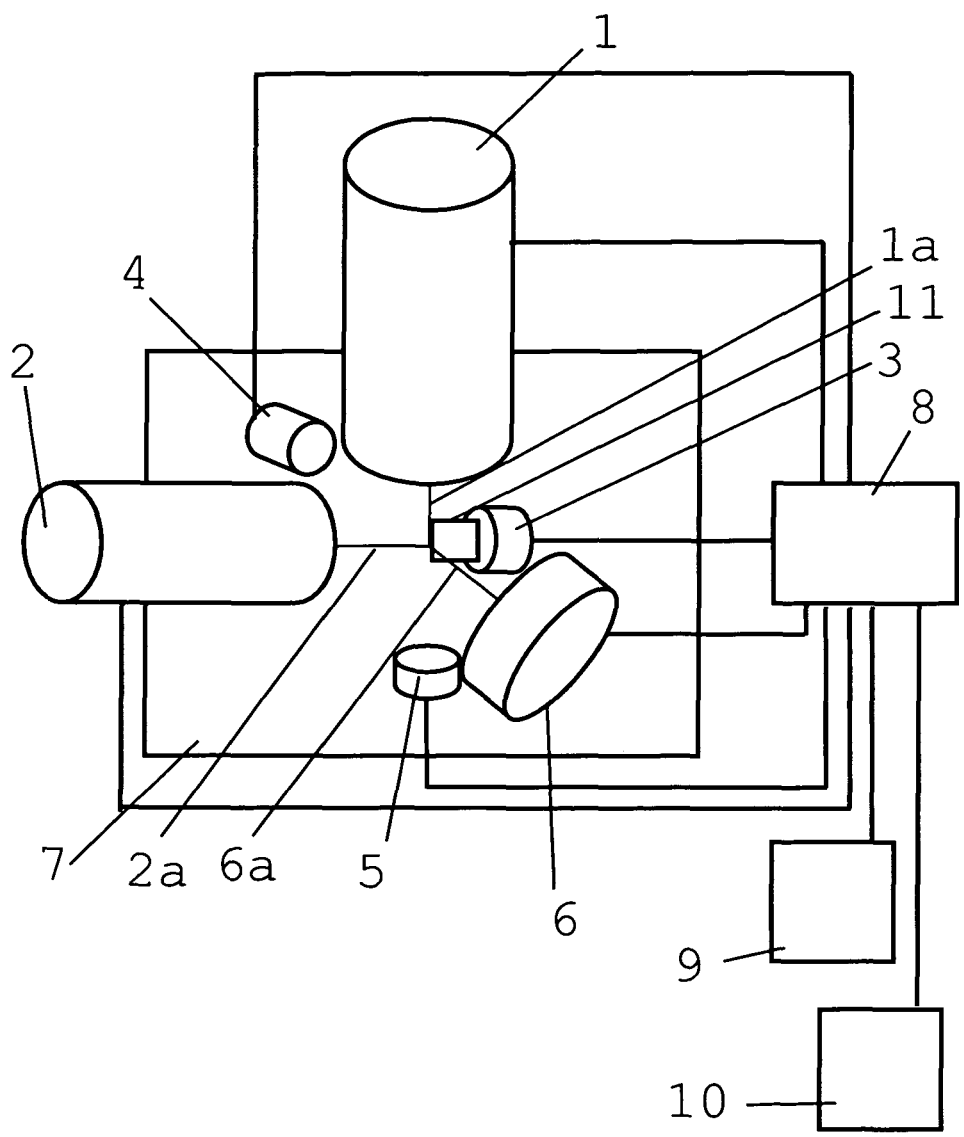
FIG. 1 is a configuration diagram of an electron microscope of an embodiment of the present invention.

As shown in FIG. 1, the electron microscope of the present embodiment is equipped with the following elements: an electron beam column 1, a focused ion beam column 2, a specimen stage 3 that supports a specimen 11, a secondary electron detector 4 that detects secondary electrons released from the specimen 11, a transmission electron detector 5 that detects transmission electrons transmitted through the specimen 11, a backscattered electron detector 6 that detects backscattered electrons 6a, a specimen chamber 7, a control unit 8 that controls the elements of the electron microscope, input means 9 for inputting measurement conditions and so forth, and a display unit 10 that displays an observation image.

Figure 2:
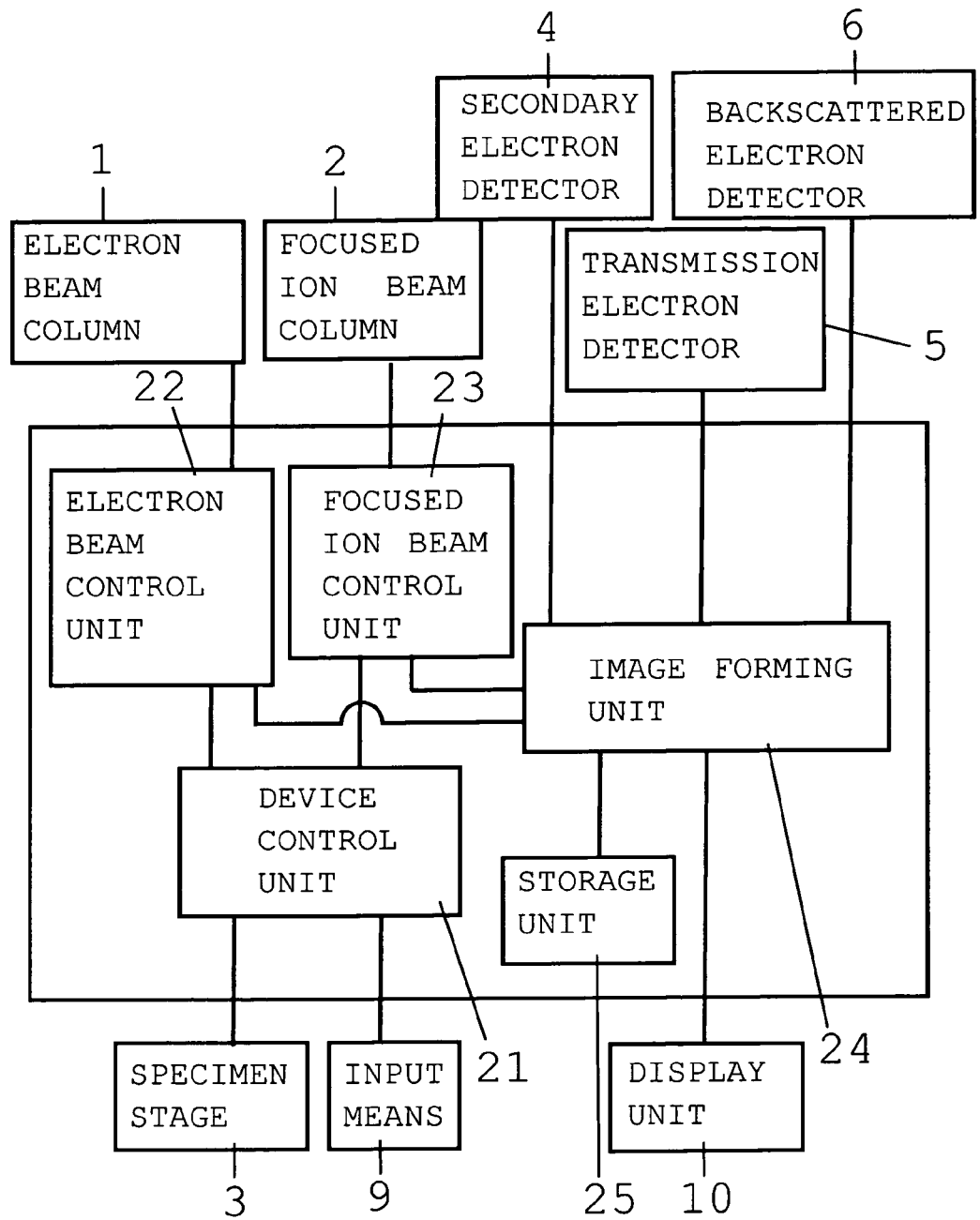
FIG. 2 is a configuration diagram of a control unit of the electron microscope of the embodiment of the present invention.

As shown in FIG. 2, the control unit 8 is equipped with: a device control unit 21 that controls each configural element of the device on the basis of input signals from the input means 9 for inputting measurement conditions and so forth with a keyboard or the like; an electron beam control unit 22 that transmits signals such as irradiation conditions, scanning regions, start of scanning, and end of scanning to the electron beam column 1 to control the electron beam 1a; and a focused ion beam control unit 23 that transmits signals such as irradiation conditions, processing regions, start of processing, and end of processing to the focused ion beam column 2 to control the focused ion beam 2a.

The control unit 8 is also equipped with: an image forming unit 24 that forms an observation image with detection signals from the secondary electron detector 4, the transmission electron detector 5, and the backscattered electron detector 6 and scanning signals from the electron beam control unit 22 and the focused ion beam control unit 23; and a storage unit 25 that stores backscattered electron detection information of multiple sections of the specimen 11 that have been formed by a focused ion beam 2a.

(1) EBSP Measurement Unit

An EBSP measurement unit is configured mainly from the electron beam column 1 and the backscattered electron detector 6. EBSP is a technique of irradiating a specimen with an electron beam and analyzing the crystal orientation from the backscattering of the electrons with which the specimen has been irradiated. When the electron beam is made incident on a specimen having a crystal structure, inelastic scattering occurs in the back and a crystal orientation-specific linear pattern (a Kikuchi pattern) resulting from Bragg diffraction inside the specimen is observed. By analyzing this Kikuchi pattern, the crystal orientation of the specimen can be obtained.

EBSP measurement uses mainly the diffraction pattern of backscattered electrons released from the specimen surface in a spread of about 70 degrees in width whose center is about 100 degrees with respect to the incident electron beam.

Figure 3A:
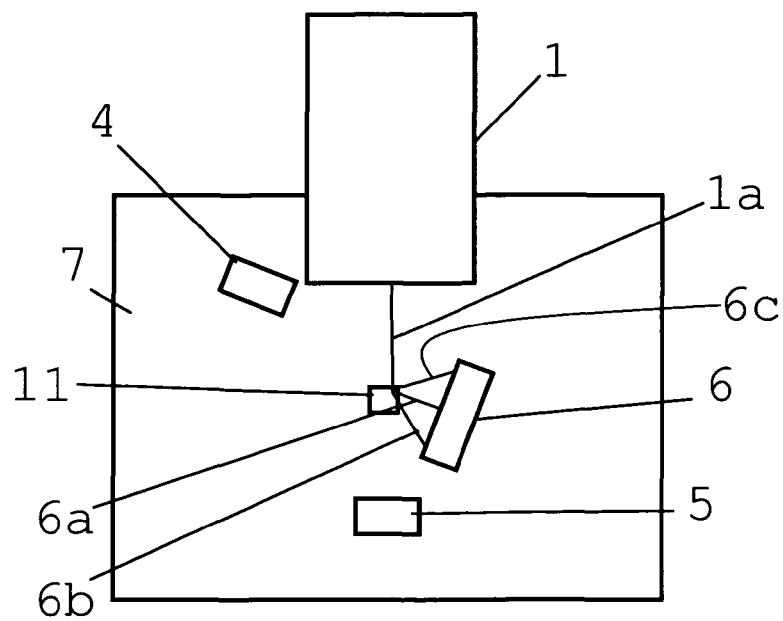
FIG. 3A is a configuration diagram of a plane formed by an electron beam and a backscattered electron detector of the electron microscope of the embodiment of the present invention.

FIG. 3A is a configuration diagram of a plane formed by an electron beam 1a and the backscattered electron detector 6 of the electron microscope pertaining to the present invention, and the normal direction of the detection plane of the backscattered electron detector 6 is placed about 100 degrees with respect to the emission direction of the electron beam 1a.

The backscattered electron detector 6 detects backscattered electrons released in a spread of about 70 degrees in width from the specimen 11. "About 70 degrees" means that, assuming that the direction in which the backscattered electrons 6a released from the specimen 11 are released is the center, the angle formed by the direction in which backscattered electrons 6b are released and the direction in which backscattered electrons 6c are released is 70 degrees.

The backscattered electron detector 6 is equipped with a fluorescent screen as its detection plane. Signals of an image projected onto the fluorescent screen are sent to the image forming unit 24. Image data can be sent from the image forming unit 24 and displayed on the display unit 10.

Further, an image analyzing program is loaded in the image forming unit 24, so that the signals from the backscattered electron detector 6 can be analyzed and an electron backscatter diffraction image showing the crystal orientation of the specimen can be formed.

(2) Focused Ion Beam Column

The focused ion beam column 2 is capable of irradiating, with the focused ion beam 2a, a region on the specimen 11 including the region irradiated by the electron beam 1a. Thus, the irradiation position can be confirmed from a secondary electron image obtained by scanning and irradiating the specimen 11 with the electron beam 1a or the focused ion beam 2a and detecting the secondary electrons that are produced with the secondary electron detector 4.

Figure 3B:
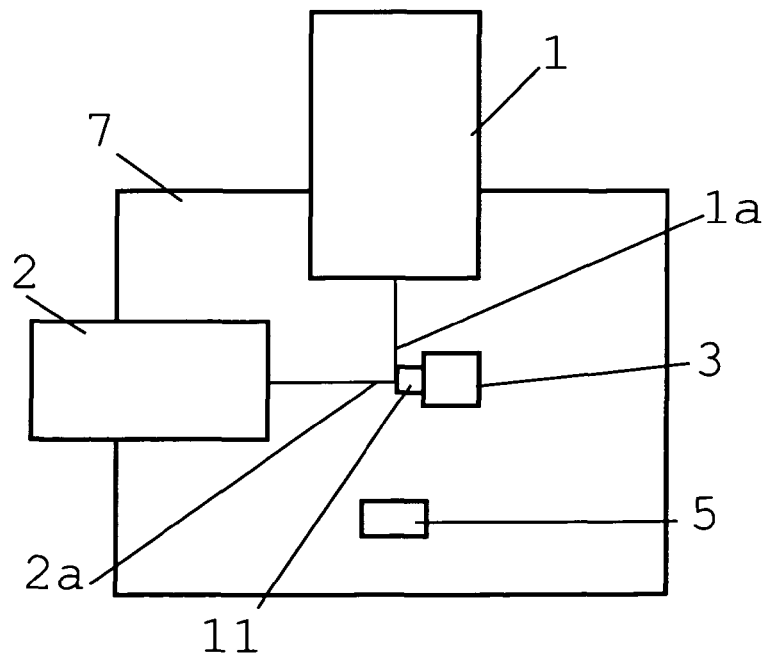
FIG. 3B is a configuration diagram of a plane formed by the electron beam and a focused ion beam of the electron microscope of the embodiment of the present invention.

Further, it is preferable for the focused ion beam column 2 to be placed in a position where the focused ion beam 2a substantially perpendicularly intersects the electron beam 1a. FIG. 3B is a configuration diagram of a plane formed by the electron beam 1a and the focused ion beam 2a of the electron microscope pertaining to the present invention, and the focused ion beam 2a and the electron beam 1a substantially perpendicularly intersect on the specimen 11.

Further, it is preferable for the direction of the backscattered electron detector 6 and the focused ion beam 2a to be substantially perpendicular. That is, the normal direction of the detection plane of the backscattered electron detector 6 forms an angle of about 100 degrees with the electron beam 1a and forms an angle of about 90 degrees with the focused ion beam 2a.

Thus, measurement can be performed without configural parts such as the columns and the detectors interfering with each other or without impeding the course of the scattered electrons released from the specimen to the detectors. Further, the specimen 11 can be irradiated with the focused ion beam 2a to forma section, and the section can be irradiated with the electron beam 1a to perform EBSP measurement. The section formed by the focused ion beam 2a is a flat surface. Then, the scattered electrons from the section can be detected accurately.

Further, because the specimen 11 is not moved between section formation by the focused ion beam 2a and EBSP measurement by the electron beam 1a, measurement can be performed efficiently.

That is, initially the specimen stage 3 is moved so as to place the specimen 11 in a predetermined position, and in section formation and EBSP measurement, it is not necessary to move the specimen 11 because the beam irradiation position is adjusted by a deflection electrode inside the focused ion beam column 2 and a deflection electrode inside the electron beam column 1.

Then, the section that has been EBSP-measured can be further processed by the focused ion beam 2a, and the new section that has been formed can be EBSP-measured.

(3) Specimen Stage

The specimen stage 3 has an axis of rotation that is substantially parallel to the focused ion beam 2a. Thus, the direction of incidence of the electron beam 1a on the section that has been formed by the focused ion beam 2a can be adjusted.

(4) Transmission Electron Detector

The specimen 11 is irradiated with the electron beam 1a, and transmission electrons released from the specimen 11 are detected by the transmission electron detector 5. A transmission electron image can be formed by the image forming unit 24 from the detection signals and the scanning signals of the electron beam 1a.

The specimen that has been EBSP-measured can be processed by the focused ion beam 2a to acquire a transmission electron image of the processed portion, so the specimen can be analyzed using the electron backscatter diffraction image and the transmission electron image.

EMBODIMENT 1

Embodiments of EBSP measurement are explained referring to FIG. 4A to FIG. 4D. The focused ion beam column 2 is placed such that the focused ion beam 2a substantially perpendicularly intersects the electron beam 1a.

FIG. 4A is a general diagram of the specimen stage 3 when the specimen stage 3 is seen from the focused ion beam column 2. The specimen stage 3 supports the specimen 11. The specimen 11 is a polycrystalline material.

The focused ion beam 2a scans and irradiates the specimen 11, and a secondary electron image of the specimen 11 surface is acquired and displayed on the display unit 10. The input means 9 is used to set a processing region on the secondary electron image.

The processing region that has been set is irradiated with the focused ion beam 2a, and etching of the specimen 11 is performed. FIG. 4B shows the specimen 11 after the etching. A section 11a is formed by the etching.

The electron beam 1a scans and irradiates the section 11a. As shown in FIG. 4C, backscattered electrons are released from the section 11a with a spread of about 70 degrees between the backscattered electrons 6b and the backscattered electrons 6c.

The backscattered electron detector 6 is placed in a position about 100 degrees with respect to the electron beam 1a. That is, assuming that the electron beam 1a and the normal direction of the detection plane of the backscattered electron detector 6 are indicated by the direction of the backscattered electrons 6a, the angle formed by the emission direction of the electron beam 1a and the direction of the backscattered electrons 6a is about 100 degrees.

Then, the backscattered electrons released in a spread of about 70 degrees between the backscattered electrons 6b and the backscattered electrons 6c whose center is the direction of the backscattered electrons 6a are detected by the backscattered electron detector 6.

That is, the backscattered electron detector 6 detects backscattered electrons released between 65 degrees (100 degrees−35 degrees) and 135 degrees (100 degrees+35 degrees) with respect to the electron beam 1a. In actuality, including installation error, backscattered electrons needed for EBSP measurement can be detected by placing the detection plane of the backscattered electron detector 6 between 60 degrees and 150 degrees with respect to the electron beam 1a.

Then, the backscattered electron image detected by the backscattered electron detector 6 is displayed on the display unit 10, the direction of the section 11a is checked, the specimen stage 3 is rotated and adjusted such that the section 11a reaches a direction optimal for measurement, and EBSP measurement is performed.

An electron backscatter diffraction image showing the crystal orientation is formed using the image analyzing program from the detection signals of the detected backscattered electrons—that is, the backscattered electron image, and is displayed on the display unit 10.

In particular, because the focused ion beam column 2 is placed such that the focused ion beam 2a substantially perpendicularly intersects the electron beam 1a, the section 11a that is substantially perpendicular to the plane formed by the electron beam 1a and the backscattered electron detector 6 can be formed without having to move the specimen stage 3.

Thus, even when the electron beam 1a scans and irradiates the section 11a to acquire a backscattered electron image at each irradiation point inside the section 11a, the angle formed by the electron beam 1a and the backscattered electron detector 6 is constant, so the backscattered electrons needed for EBSP measurement can be detected without having to move the specimen stage 3.

EMBODIMENT 2

An embodiment where substantially parallel multiple sections are formed towards the interior of the specimen 11 by the focused ion beam 2a and where each of those sections is irradiated with the electron beam 1a to perform EBSP measurement is explained.

EBSP measurement of the section 11a is performed, and the backscattered electron detection information is stored in the storage unit 25.

As shown in FIG. 4D, a region including the section 11a is etched to form a new section 11b. The section 11b is substantially parallel to the section 11a and is a section deeper inside the specimen 11.

The new section 11b is irradiated with the electron beam 1a to perform EBSP measurement. The backscattered electron detection information of the section 11b is stored in the storage unit 25.

Moreover, a new section 11c is formed. By repeatedly performing this process, EBSP measurement of multiple sections of the interior of the specimen 11 is performed.

Reconstruction processing is performed by the image forming unit 10 on the backscattered electron detection information of the multiple sections stored in the storage unit 25.

In the reconstruction processing, a three-dimensional crystal orientation mapping of the specimen 11 is displayed from the distance between the multiple sections etched by the focused ion beam 2a, that is, the processing width in which etching was performed and the backscattered electron detection information.

The three-dimensional crystal orientation mapping is a distribution where the multiple backscattered electron images or the electron backscatter diffraction images processed by the image analyzing program are superposed substantially parallel to each other and displayed in consideration of the distance between the sections.

Thus, the crystal orientation of the interior of the specimen 11 can be investigated.

EMBODIMENT 3

An embodiment where the specimen is processed to acquire a transmission electron image after EBSP measurement of the section has been performed is explained.

A section is formed in the specimen 11 by the focused ion beam 2a, and EBSP measurement of the section is performed. Next, the focused ion beam 2a is irradiated to the specimen 11 to make a lamella having a thickness through which the electron beam 1a is transmittable.

The specimen stage 3 is rotated and placed such that the lamella surface becomes substantially perpendicular to the electron beam 1a. The lamella is irradiated with the electron beam 1a, and transmission electrons released from the lamella are detected by the transmission electron detector 5. The transmission electron detector 5 is placed in the emission direction of the electron beam 1a.

A transmission electron image is formed by the image forming unit 24 from the detection signals detected by the transmission electron detector 5 and the scanning signals of the electron beam 1a and is displayed on the display unit 10.

By comparing the transmission electron image with the crystal orientation information of the section obtained by EBSP measurement, the crystal orientation of the specimen can be analyzed from many angles.

What is claimed is:

1. An electron microscope comprising:
an electron beam column for irradiating a specimen with an electron beam;
a specimen stage configured to support the specimen;
a focused ion beam column for irradiating the specimen with a focused ion beam and forming a section of the specimen to be analyzed; and
a scattered electron detector configured and positioned to detect backscattered electrons released in a spread between 65 degrees and 135 degrees with respect to the electron beam from the surface of the section by irradiation of the section with the electron beam,
wherein the specimen stage is positioned spaced from the axis of the electron beam,
wherein the scattered electron detector has a detection plane on which the backscattered electron are incident, and
wherein the focused ion beam column is positioned such that
a direction of the focused ion beam is substantially perpendicular to a direction normal to the detection plane, and
the focused ion beam substantially perpendicularly intersects the electron beam.

2. The electron microscope according to claim 1, wherein the scattered electron detector is configured to detect a Kikuchi pattern of the backscattered electrons.

3. The electron microscope according to claim 1, wherein an angle formed by the scattered electron detector and the electron beam is 60 degrees to 150 degrees.

4. The electron microscope according to claim 1, wherein the focused ion beam is capable of irradiating the region irradiated by the electron beam.

5. The electron microscope according to claim 1, wherein the specimen stage has an axis of rotation that is substantially parallel to the focused ion beam.

6. The electron microscope according to claim 1, further comprising a storage unit that stores backscattered electron detection information of mutually substantially parallel multiple sections of the specimen that have been formed by the focused ion beam.

7. The electron microscope according to claim 1, further comprising a transmission electron detector for detecting transmission electrons released from the specimen in the emission direction of the electron beam.

8. The electron microscope according to claim 1, wherein the direction normal to the detection plane forms an angle of about 100 degrees with the electron beam.

9. The electron microscope according to claim 1, wherein the scattered electron detector is configured and positioned to detect backscattered electrons released between 65 degrees and 135 degrees with respect to the direction of the electron beam.

10. A specimen analyzing method comprising:
a section forming step of irradiating a specimen with a focused ion beam in a first direction and forming a section of the specimen to be analyzed;
a detecting step of irradiating the section with an electron beam in a second direction and detecting backscattered electrons released in a spread between 65 degrees and 135 degrees with respect to the electron beam from the surface of the section in response to irradiating the section with the electron beam by using a detector having a detection plane on which the backscattered electrons are incident; and
an image acquiring step of acquiring a backscattered electron image of the section from detection signals of the backscattered electrons,
wherein the first direction is substantially perpendicular to both the second direction and a normal direction of the detection plane.

11. The specimen analyzing method according to claim 10, wherein the section forming step and the detecting step are implemented inside a specimen chamber.

12. The specimen analyzing method according to claim 10, wherein in the detecting step, the electron beam scans and irradiates the section.

13. The specimen analyzing method according to claim 10, wherein the section forming step and the detecting step are repeatedly implemented to acquire detection signals of backscattered electrons of mutually substantially parallel multiple sections.

14. A specimen analyzing method of acquiring crystal orientation information of the multiple sections from the detection signals detected by the specimen analyzing method according to claim 13 and combining the crystal orientation information to acquire a three-dimensional crystal orientation map of the specimen.

15. The specimen analyzing method according to claim 10, further comprising
- a lamella making step of processing the specimen into a lamella with the focused ion beam and
- a transmission electron detecting step of irradiating the lamella with the electron beam and detecting transmission electrons from the lamella.

16. The specimen analyzing method according to claim 15, wherein the lamella is analyzed using the backscattered electron image acquired in the image acquiring step and a transmission electron image acquired in the transmission electron detecting step.

* * * * *